United States Patent [19]

Daniels et al.

[11] Patent Number: 5,670,482
[45] Date of Patent: Sep. 23, 1997

[54] NEUROPEPTIDE Y ANTAGONISTS

[75] Inventors: Alejandro Jose Daniels; Dennis Heyer; Antonio Landavazo; Johann Jakob Leban, all of Durham; Andreas Spaltenstein, Raleigh, all of N.C.

[73] Assignee: Glaxo Wellcome Inc., Research Triangle Park, N.C.

[21] Appl. No.: 360,706

[22] PCT Filed: Jun. 18, 1993

[86] PCT No.: PCT/GB93/01297

§ 371 Date: Feb. 17, 1995

§ 102(e) Date: Feb. 17, 1995

[87] PCT Pub. No.: WO94/00486

PCT Pub. Date: Jan. 6, 1994

[30] Foreign Application Priority Data

Jun. 20, 1992 [GB] United Kingdom ............... 9213215

[51] Int. Cl.$^6$ .................... A61K 38/04; A61K 38/16
[52] U.S. Cl. .................... 514/12; 514/15; 530/324; 530/328
[58] Field of Search .................... 530/324, 328; 514/12, 15

[56] References Cited

U.S. PATENT DOCUMENTS

| | | | |
|---|---|---|---|
| 4,839,343 | 6/1989 | Waeber et al. | 514/12 |
| 4,891,357 | 1/1990 | Kalra | 514/12 |
| 4,897,445 | 1/1990 | Coy et al. | 525/54.11 |
| 5,128,332 | 7/1992 | Siren et al. | 514/103 |
| 5,284,839 | 2/1994 | Siren et al. | 514/103 |
| 5,328,899 | 7/1994 | Boublik et al. | 514/13 |
| 5,330,979 | 7/1994 | Siren et al. | 514/103 |

FOREIGN PATENT DOCUMENTS

| | | |
|---|---|---|
| 124 314 | 11/1984 | European Pat. Off. |
| 338 436 | 10/1989 | European Pat. Off. |
| 355 793 | 2/1990 | European Pat. Off. |
| 355 794 | 2/1990 | European Pat. Off. |
| 38 11 193 | 10/1989 | Germany |
| 1006 294 | 1/1989 | Japan |
| 89 02460 | 3/1989 | WIPO |

OTHER PUBLICATIONS

Beck–Sickinger et al., "Structure–activity Relationships of Neuropeptide Y," Peptides, Proceedings of the Twelfth American Peptide Symposium, 17–19 (Jun. 16–21, 1991).
Forest et al., "Structural Study of the N–Terminal Segment of Neuropeptide Tyrosine," J. Med. Chem., 33(6), 1615–1619 (1990).

*Primary Examiner*—Cecilia J. Tsang
*Assistant Examiner*—Anish Gupta
*Attorney, Agent, or Firm*—LaVonda E. DeWitt; Robert T. Hrubiec

[57] ABSTRACT

The present invention relates to peptides which show improved Neuropeptide Y antagonism to pharmaceutical compositions containing such peptides and their use.

16 Claims, No Drawings

SEQUENCE LISTING ( 1 ) GENERAL INFORMATION:

( v i i ) NUMBER OF SEQUENCES: 18

( 2 ) INFORMATION FOR SEQ ID NO: 1:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa is Ile, Ile Tyr, or desNH2TyrIle"

( i x ) FEATURE:
    ( A ) NAME/KEY: Modified-site
    ( B ) LOCATION: 2
    ( D ) OTHER INFORMATION:/note="Xaa is Asn, Asp, Cys, Dpr, Glu, or Gly"

( i x ) FEATURE:
    ( A ) NAME/KEY: Modified-site
    ( B ) LOCATION: 3
    ( D ) OTHER INFORMATION: /note= "Xaa is Leu, Pro, or 3,4- dehydroPro"

( i x ) FEATURE:
    ( A ) NAME/KEY: Modified-site
    ( B ) LOCATION: 4
    ( D ) OTHER INFORMATION: /note= "Xaa is Aib, Asp, Cys, Dpr, Glu, Gly, Ile, Orn, Tyr, or O-mehtylThr"

( i x ) FEATURE:
    ( A ) NAME/KEY: Modified-site
    ( B ) LOCATION: 5
    ( D ) OTHER INFORMATION: /note= "Xaa is Phe, Tyr, or O-(2,6- dichlorobenzyl)Tyr"

( i x ) FEATURE:
    ( A ) NAME/KEY: Modified-site
    ( B ) LOCATION: 7
    ( D ) OTHER INFORMATION: /note= "Xaa is Phe or Leu"

( i x ) FEATURE:
    ( A ) NAME/KEY: Modified-site
    ( B ) LOCATION: 9
    ( D ) OTHER INFORMATION: /note= "Xaa is Phe, Tyr, or O-(2,6- dichlorobenzyl)Tyr"

( x i ) SEQUENCE DESCRIPTION: SEQ ID NO: 1:

```
Xaa  Xaa  Xaa  Xaa  Xaa  Arg  Xaa  Arg  Xaa
1                   5
```

( 2 ) INFORMATION FOR SEQ ID NO: 2:

( i ) SEQUENCE CHARACTERISTICS:
        ( A ) LENGTH: 9 amino acids
        ( B ) TYPE: amino acid
        ( C ) STRANDEDNESS: double
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note= "Xaa is Orn"

( x i ) SEQUENCE DESCRIPTION: SEQ ID NO: 2:

```
Ile  Glu  Pro  Xaa  Tyr  Arg  Leu  Arg  Tyr
1                   5
```

( 2 ) INFORMATION FOR SEQ ID NO: 3:

( i ) SEQUENCE CHARACTERISTICS:
        ( A ) LENGTH: 9 amino acids
        ( B ) TYPE: amino acid
        ( C ) STRANDEDNESS: double
        ( D ) TOPOLOGY: linear ( i i ) MOLECULE TYPE: peptide ( i x ) FEATURE:

(A) NAME/KEY: Modified-site
(B) LOCATION: 4
(D) OTHER INFORMATION: /note= "Xaa is Orn"

(xi) SEQUENCE DESCRIPTION: SEQ ID NO: 3:

Ile Asp Pro Xaa Tyr Arg Leu Arg Tyr
1               5

(2) INFORMATION FOR SEQ ID NO: 4:

(i) SEQUENCE CHARACTERISTICS:
    (A) LENGTH: 9 amino acids
    (B) TYPE: amino acid
    (C) STRANDEDNESS: double
    (D) TOPOLOGY: linear (ii) MOLECULE TYPE: peptide (ix) FEATURE:
    (A) NAME/KEY: Modified-site
    (B) LOCATION: 4
    (D) OTHER INFORMATION: /note= "Xaa is Dpr"

(xi) SEQUENCE DESCRIPTION: SEQ ID NO: 4:

Ile Glu Pro Xaa Tyr Arg Leu Arg Tyr
1               5

(2) INFORMATION FOR SEQ ID NO: 5:

(i) SEQUENCE CHARACTERISTICS:
    (A) LENGTH: 9 amino acids
    (B) TYPE: amino acid
    (C) STRANDEDNESS: double
    (D) TOPOLOGY: linear (ii) MOLECULE TYPE: peptide (ix) FEATURE:
    (A) NAME/KEY: Modified-site
    (B) LOCATION: 2
    (D) OTHER INFORMATION: /note= "Xaa is Dpr"

(xi) SEQUENCE DESCRIPTION: SEQ ID NO: 5:

Ile Xaa Pro Asp Tyr Arg Leu Arg Tyr
1               5

(2) INFORMATION FOR SEQ ID NO: 6:

(i) SEQUENCE CHARACTERISTICS:
    (A) LENGTH: 9 amino acids
    (B) TYPE: amino acid
    (C) STRANDEDNESS: double
    (D) TOPOLOGY: linear (ii) MOLECULE TYPE: peptide (xi) SEQUENCE DESCRIPTION: SEQ ID NO: 6:

Ile Cys Pro Cys Tyr Arg Leu Arg Tyr
1               5

(2) INFORMATION FOR SEQ ID NO: 7:

(i) SEQUENCE CHARACTERISTICS:
    (A) LENGTH: 9 amino acids
    (B) TYPE: amino acid
    (C) STRANDEDNESS: double
    (D) TOPOLOGY: linear (ii) MOLECULE TYPE: peptide (ix) FEATURE:
    (A) NAME/KEY: Modified-site (B) LOCATION: 4
        (D) OTHER INFORMATION: /note= "Xaa is Dpr"

(xi) SEQUENCE DESCRIPTION: SEQ ID NO: 7:

Ile  Asp  Pro  Xaa  Tyr  Arg  Leu  Arg  Tyr
    1                     5

(2) INFORMATION FOR SEQ ID NO: 8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is Aib"

(xi) SEQUENCE DESCRIPTION: SEQ ID NO: 8:

Ile  Asn  Pro  Xaa  Tyr  Arg  Leu  Arg  Tyr
    1                     5

(2) INFORMATION FOR SEQ ID NO: 9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is O-methylThr"

(xi) SEQUENCE DESCRIPTION: SEQ ID NO: 9:

Ile  Asn  Pro  Xaa  Tyr  Arg  Leu  Arg  Tyr
    1                     5

(2) INFORMATION FOR SEQ ID NO: 10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is Aib"

(ix) FEATURE:
        (A) NAME/KEY: Modified-site
        (B) LOCATION: 5
        (D) OTHER INFORMATION: /note= "Xaa is
            O-(2,6- dichlorobenzyl)Tyr"

(xi) SEQUENCE DESCRIPTION: SEQ ID NO: 10:

Ile  Asn  Pro  Xaa  Xaa  Arg  Leu  Arg  Tyr
    1                     5

(2) INFORMATION FOR SEQ ID NO: 11:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 9
    ( D ) OTHER INFORMATION: /note= "Xaa is
        O-(2,6- dichlorobenzyl)Tyr"

( x i ) SEQUENCE DESCRIPTION: SEQ ID NO: 11:

Ile Asn Pro Ile Tyr Arg Leu Arg Xaa
1               5

( 2 ) INFORMATION FOR SEQ ID NO: 12:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 5
    ( D ) OTHER INFORMATION: /note= "Xaa is
        O-(2,6- dichlorobenzyl)Tyr"

( x i ) SEQUENCE DESCRIPTION: SEQ ID NO: 12:

Ile Asn Pro Ile Xaa Arg Leu Arg Tyr
1               5

( 2 ) INFORMATION FOR SEQ ID NO: 13:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 13:

Ile Asn Pro Ile Phe Arg Leu Arg Tyr
1               5

( 2 ) INFORMATION FOR SEQ ID NO: 14:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /note= "Xaa is 3,4-dehydroPro"

( x i ) SEQUENCE DESCRIPTION: SEQ ID NO: 14:

Ile Asn Xaa Ile Tyr Arg Leu Arg Tyr
1               5

( 2 ) INFORMATION FOR SEQ ID NO: 15:

(i) SEQUENCE CHARACTERISTICS:
    (A) LENGTH: 9 amino acids
    (B) TYPE: amino acid
    (C) STRANDEDNESS: double
    (D) TOPOLOGY: linear (ii) MOLECULE TYPE: peptide (xi) SEQUENCE DESCRIPTION: SEQ ID NO: 15:

Ile Asn Pro Cys Tyr Arg Leu Arg Tyr
1               5

(2) INFORMATION FOR SEQ ID NO: 16:

(i) SEQUENCE CHARACTERISTICS:
    (A) LENGTH: 9 amino acids
    (B) TYPE: amino acid
    (C) STRANDEDNESS: double
    (D) TOPOLOGY: linear (ii) MOLECULE TYPE: peptide (xi) SEQUENCE DESCRIPTION: SEQ ID NO: 16:

Ile Cys Pro Ile Tyr Arg Leu Arg Tyr
1               5

(2) INFORMATION FOR SEQ ID NO: 17:

(i) SEQUENCE CHARACTERISTICS:
    (A) LENGTH: 9 amino acids
    (B) TYPE: amino acid
    (C) STRANDEDNESS: double
    (D) TOPOLOGY: linear (ii) MOLECULE TYPE: peptide (ix) FEATURE:
    (A) NAME/KEY: Modified-site
    (B) LOCATION: 4
    (D) OTHER INFORMATION: /note= "Xaa is 2,6-diaminopimelic acid L,D"

(xi) SEQUENCE DESCRIPTION: SEQ ID NO: 17:

Ile Asn Pro Xaa Tyr Arg Leu Arg Tyr
1               5

(2) INFORMATION FOR SEQ ID NO: 18:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 18:

Tyr Ile Asn Leu Ile Tyr Arg Leu Arg Tyr
1               5                   10

NEUROPEPTIDE Y ANTAGONISTS

This application is a 371 of PCT/GB93/01297, filed Jun. 18, 1993.

FIELD OF THE INVENTION

The present invention relates to peptides which show improved Neuropeptide Y antagonism, to pharmaceutical compositions containing such peptides and to their use in animal and human medicine.

Neuropeptide Y (NPY) is a 36 residue amidated peptide first isolated from brain tissue in 1982 (Tatemoto K., Carlquist M. and Mutt V., Nature 296; 659–660, 1982). The peptide is widely distributed throughout the mammalian central nervous system and the peripheral sympathetic nervous system; in the latter it is colocalised with norepinephrine. Peripheral administration of NPY induces vasoconstriction in many vascular beds and also potentiates the vasoconstriction induced by norepinephrine, and other vasoactive substances, in vessels where NPY does not have a direct effect. NPY functions in the brain as an appetite stimulant and promotes release of prolactin growth hormone and leutinizing hormone. NPY is known to elicit its effect by binding to receptors located in the central and peripheral nervous system. EPO 355 794 and DE 38 11 193 describe derivatives of NPY which may bind to such NPY receptors and act as antagonists of NPY activity.

SUMMARY OF THE INVENTION

A class of peptides has now been found which are effective NPY antagonists. These antagonists suppress the action of endogenous NPY and are therefore useful in cardiovascular disorders, hypertension and hypertensive crisis, vasospasm, cerebral or coronary vasospasm (eg. stroke), eating disorders, depression and also in glaucoma. Such compounds are particularly suitable for use in combination with angiotensin converting enzyme (ACE) inhibitors and calcium antagonists.

DETAILED DESCRIPTION OF THE INVENTION

The present invention provides a peptide of formula (I), or a multimer thereof or a salt thereof:

$$R_1-X_5ArgX_6ArgX_5-R_2 \quad (SEQ. ID.No.1) \ (I)$$

there

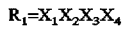

in which $X_1$=Ile or TyrIle, or desNH$_2$TyrIle
$X_2$=Asn,Asp,Cys,Dpr,Glu or Gly
$X_3$=Leu,Pro or 3,4-DehydroPro
$X_4$=Aib,Asp,Cys,Dpr,Glu,Gly,Ile,Orn,Tyr or O-MethylThr
$X_5$=Phe,Tyr or [O-(2,6-Dichlorobenzyl)Tyr]
$X_6$=Phe or Leu where $R_2$=—(CH$_2$)$_n$CH$_3$, —(CH$_2$)$_n$NH$_2$ or

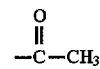

in which n=0–4.

A multimer according to the present invention includes a dimer. Such normally occur when peptides containing Gly residues are bridged at the alpha position by a group selected from the following;

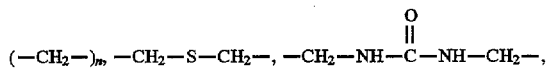

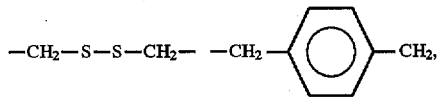

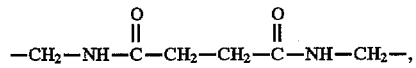

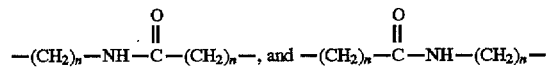

in which n is as defined herein. Alternatively, such multimers may also occur when peptides are lactam bridged. Such multimers can contain one or more such bridges, preferably two.

It is preferred that a peptide of the invention is used in the form of a dimer.

A salt of a peptide or a multimer of the invention is also included within the scope of the present invention. Such a salt is prepared according to any of the methods well known in the art.

A pharmaceutically acceptable salt of a peptide or a multimer of the invention is also included within the scope of the present invention. Suitable pharmaceutically acceptable salts include acid addition salts when the peptide is sufficiently basic i.e., contains one or more basic residues.

A suitable pharmaceutically acceptable acid addition salt of a peptide of the invention may be formed with an inorganic acid, for example hydrochloric acid, hydrobromic acid, sulphuric acid or phosphoric acid, or with an organic acid, for example acetic acid, citric acid, maleic acid, fumaric acid, succinic acid, tartaric acid or trifluoroacetic acid.

Preferred examples of $X_2$ include Cys and Glu.
Preferred examples of $X_3$ include Pro.
Preferred examples of $X_4$ include Cys Dpr and Orn.
Preferred examples of $X_5$ include Tyr.
Preferred examples of $X_6$ include Leu.
Preferred examples of $R_2$ include —(CH$_2$)$_n$NH$_2$ in particular wherein n is 0.

A preferred sub-class of a peptide of formula (I), or a multimer thereof, or a salt thereof, is that wherein $X_5$ is Tyr, $X_6$ is Leu, and $R_1$ and $R_2$ have the meaning described above.

The following abbreviations for amino acid residues are used throughout:

Aib for 2-methyl alanine, Arg for arginine, Asn for asparagine, Asp for aspartic acid, Cys for cysteine, Dpr for diaminoproprionic acid, Glu for glutamic acid, Gly for glycine, Ile for isoleucine, Leu for leucine, Orn for ornithine, Phe for phenylalanine, Pro for proline, Thr for threonine and Tyr for tyrosine.

The present invention relates particularly to the following peptides:

IleGluProOrnTyrArgLeuArgTyr-NH$_2$,Cyclic(2,4'),(2',4)-Diamide (SEQ.ID.No:2)
IleAspProOrnTyrArgLeuArgTyr-NH$_2$,Cyclic(2,4'),(2',4)-Diamide (SEQ.ID.No:3)
IleGluProDprTyrArgLeuArgTyr-NH$_2$,Cyclic(2,4'),(2',4)-Diamide (SEQ.ID.No:4)
IleAspProDprTyrArgLeuArgTyr-NH$_2$,Cyclic(2,4'),(2',4)-Diamide (SEQ.ID.No:7)
IleDprProAspTyrArgLeuArgTyr-NH$_2$,Cyclic(2,4'),(2',4)-Diamide (SEQ.ID.No:5) and
IleCysProCysTyrArgLeuArgTyr-NH$_2$,Cyclic (2,2'),(4,4')-Disulfide Dimer, (SEQ.ID.No:6)
IleCysProCysTyrArgLeuArgTyr-NH$_2$,Cyclic (2,4'),(4,2')-Disulfide Dimer (SEQ.ID.No:6)
or a pharmaceutically acceptable salt thereof.

The invention relates most particularly to the following peptides:
IleGluProOrnTyrArgLeuArgTyr-NH$_2$,Cyclic(2,4'),(2',4)-Diamide (SEQ.ID.No:2)
IleAspProOrnTyrArgLeuArgTyr-NH$_2$,Cyclic(2,4'),(2',4)-Diamide (Seq.ID.No:3)
IleGluProDprTyrArgLeuArgTyr-NH$_2$,Cyclic(2,4'),(2',4)-Diamide (SEQ.ID.No:4)
IleAspProDprTyrArgLeuArgTyr-NH$_2$,Cyclic(2,4'),(2',4)-Diamide (SEQ.ID.No:7) and
IleDprProAspTyrArgLeuArgTyr-NH$_2$,Cyclic(2,4')(2',4)-Diamide (SEQ.ID.No:5)
or a pharmaceutically acceptable salt thereof.

According to the present invention there is also provided a method for the treatment of cardiovascular disorders, hypertension, hypertensive crisis, vasospasm, cerebral or coronary vasospasm (eg. stroke), eating disorders, depression and also glaucoma, which comprises administering to a mammal e.g. human, a therapeutically effective, non-toxic amount of a peptide or a multimer or a salt according to the present invention. There is also provided the use of a peptide or a multimer or a salt according to the present invention in the manufacture of a medicament for the treatment of any of the above-mentioned conditions.

Peptides of formula (I) of the present invention wherein X$_3$ is Leu also exhibit agonistic properties. These agonists can mimick or enhance the actions of endogenous NPY and are therefore useful in treating conditions requiring activation of NPY receptors, for example as vasoconstrictors. More particularly they are useful in the treatment of hypotension, vasodilation, septic shock, rhynitis, cystic fibrosis, anxiety and in the protection against nephrotoxicity.

According to a further feature of the invention there is provided a pharmaceutical composition which comprises a peptide of the present invention, or a multimer thereof, or a pharmaceutically acceptable salt thereof, in association with a pharmaceutically acceptable diluent or carrier.

The composition may be in a form suitable for oral use, for example a tablet, capsule, aqueous or oily solution, suspension or emulsion; for nasal use, for example, a snuff, nasal spray or nasal drops; for optical use, for example, eye drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients. However, in the case of a composition for oral administration, it may be convenient for the composition to include a coating to protect the peptide active ingredient from the degradative actions of enzymes in the stomach.

An oral composition of the invention is, in unit dosage, for example a tablet or capsule which contains from 2.5 to 500 mg, and preferably 1 to 200 mg, of peptide in each unit dose, or one suitable for parenteral administration which contains from 0.5 to 100 mg of peptide per ml, and preferably 1 to 10 mg of peptide per ml of solution.

A parenteral composition is preferably a solution in isotonic saline or isotonic dextrose buffered if necessary to a pH of 5 to 9. Alternatively, the parenteral composition may be one designed for slow release in which case the amount of polypeptide per unit dose is in general greater than that required when a conventional injectable formulation is used. A preferred slow release formulation is, for example, a continuous release formulation, for example a formulation of the type described in U.S. Pat. No. 4,767,628 and U.S. Pat. No. 5,004,602 which are incorporated herein in their entirety. A preferred slow release parenteral formulation contains from 10 to 100 mg of polypeptide per unit dose. Another preferred slow release formulation is a microencapsulated polypeptide using a biodegradable biocompatible copolymer.

These preparations are preferably administered intravenously, although administration may also be effected by means of subcutaneous, intramuscular, or intradermal injection.

Medicaments suitable for transdermal administration may take the form of an optionally buffered aqueous solution of a compound of the general formula, or a pharmaceutically acceptable salt thereof and may be delivered by passive diffusion or by electrically-assisted transport, for example, iontophoresis (see, for example, Pharmaceutical Research 3(6), 318 (1986)).

The composition of the invention will normally be administered such that a daily oral dose will be from 0.1 mg/kg, to 50 mg/kg of bodyweight and most preferably from 0.5 mg/kg to 10 mg/kg and a daily parenteral dose, will be from 20 micrograms/kg to 10 mg/kg more preferably from 50 micrograms/kg to 2 mg/kg.

The peptides of the invention may be prepared by any process well known in the art of peptide chemistry to be applicable to the synthesis of analogous compounds. Thus, for example, a polypeptide of the invention may be obtained by procedures analogous to those disclosed in "Solid Phase Peptide Synthesis" by Stewart and Young (published by the Pierce Chemical Company, Illinois, 1984), "Principles of Peptide Synthesis" (published by Springer-Verlag, Berlin, 1984), "Practice of Peptide Synthesis" (published by Springer-Verlag, Berlin, 1984), and "The Synthesis of a Tetrapeptide" (J.Am.Chem.Soc., 83 2149(1963)).

The multimers of the invention may be prepared by the methods described hereinafter or by any process well known in the art of peptide chemistry.

The salts of the invention may be prepared by any process well known in the art.

PEPTIDE SYNTHESIS AND PURIFICATION

The peptides were synthesized using an improved version of the solid phase method described by R. B. Merrifield, "Solid Phase Peptide Synthesis I. The Synthesis of a Tetrapeptide", J.Am.Chem., 83, 2149 (1963), using an Applied Biosystems Model 430A peptide synthesizer.

The MBHA resin was obtained from Advanced Chemtech of Louisville, Ky. The BOP reagent was received from Richelieu Biotechnologies in St-Hyacinthe, Quebec, Canada. The majority of the natural Boc- and Fmoc-protected amino acids utilized were obtained from the Bachem Chemical Co. of Torrance, Calif., including Boc-Cys(4MeBzl), Boc-Phe, Boc-His(CBZ), Boc-Ile.1/2H$_2$O, Boc-Leu.H$_2$O, Boc-Asn(Xan), Boc-Nle, Boc-Pro Boc-Arg (Tos), Boc-Trp, Boc-Tyr(2-Br-CBZ), Fmoc-Cys(Trt), Fmoc-Ile, Fmoc-Leu, Fmoc-Asn(Trt), Fmoc-Pro, Fmoc-Arg (PMC), Fmoc-Tyr(Ot-butyl), and Fmoc-Tyr(O-2,6-dichlorobenzyl), Bachem of California also supplied Boc-6-aminocaproic acid (Aha) and Boc-3,4-dehydroproline. The O-methylhomoserine (MeOThr) was supplied by Biohellas S.A. of Greece. The Boc-aminoisobutyric acid (Aib) and parahydroxyphenylpropionic acid [(de-NH$_2$)Y] was obtained from the Fluka Chemical Corp. of Ronkonkoma, N.Y. Boc-benzothienylalanine (BzThiAla) was obtained from SyntheTech of Albany, Oreg. The Aldrich Chemical Co. of Milwaukee, Wis. supplied 1-methylimidazole, phenylpro-pionic acid [(de-NH$_2$)F], and 3,4-dichlorophenylacetic acid. Boc-Asp(OFm) and 1-Naphthyl-3-alanine were obtained from Bachem Bioscience Inc. of Philadelphia, Pa.

Method A: Peptide Synthesis Using t-Boc Chemistry

Most peptides were synthesized by the Boc-protection procedure as follows:

Boc-protected amino acids were coupled to the MBHA (methyl benzhydryl) resin (Advanced Chem.Tech, Louiseville, Ky. Catalog 1990–91 p129, SA5016) using a programme to suit a BOP coupling procedure, as described by Dung Le-Nguyen, Annie Heik, and Bertrand Castro, J.Chem.Soc., Perkins Trans. 1, 1914 (1987). The coupling protocol involved dissolving 1 mMole of Boc-protected amino acid, 1 mMole BOP, and 1 mL of 1M 1-methylimidazole in 7 mL of DMF. The mixture was added to 0.5 mMoles of resin, mixed for 1 hour, and filtered. This procedure was performed automatically in an Applied Biosystems 430A peptide synthesizer with the Boc-protected amino acid and BOP filled in the amino acid cartridge using a short programme routine to perform the above coupling steps. Afterwards, a series of DMF and CH$_2$Cl$_2$ washes and TFA deprotection steps was performed in an Applied Biosystems model 430A peptide Synthesizer using programmes supplied by the manufacturer (Applied Biosystems. Foster City, Calif.) and this procedure was automatically repeated for each desired amino acid until the desired sequence is assembled in the synthesizer.

After the peptide was assembled on the resin, it was deblocked and cleaved from the resin with liquid HF containing 10% anisole, in a variation of the method described by S. Sakakibara, et al., in Bull.Chem.Soc.Jap., 40, 2164 (1967). The peptide and resin were next washed with ethyl acetate and the peptide was extracted from the resin with an aqueous 1–10% acetic acid solution. The peptide solution was then lyophilized to obtain the dry, solid peptide.

Peptides containing disulfide bridges were prepared as described in the Examples.

Method B: Peptide Synthesis Using Fmoc Chemistry

Several peptides contained functionalities that were labile against strong acid and were synthesized by the Fmoc-protection procedure. The peptides were assembled by an automated method on a Milligen 9050 peptide sythesiser using BOP as the coupling reagent. A 4-(2',4'-dimethoxyphenyl-FMOc-aminomethyl)-phenoxy resin ("Rink resin") (Bachem Torrance, Calif., Catalogue 1991–92 p136 RMIS70), (2.2 g, 0.198 mM) was combined with 3.2 g of acid washed glass beads (Sigma, 250-212 micron size) and loaded into the flow-through reaction vessel of the peptide synthesizer. The appropriate side chain protected FMOC amino acids were placed into individual cartridges in 0.8 mmole allotments. BOP Reagent (354 mg, 0.8 mmoles) and 1-Hydroxy-benzotria-zole (122 mg, 0.9 mmoles) were added to each cartridge before sealing. The automated synthesis required about 20 h. The peptides were cleaved from the resin using a standard trifluoroacetic acid method. The resin/glass bead mixture was introduced into a plastic screw-top Sarstedt tube (50 mL capacity). To it was added 10 mL of the following solution: 9 mL of TFA, 0.5 mL of thioanisole, 0.3 mL of ethanedithiol, and 0.2 mL of anisole. This cleavage reaction mixture was allowed to stand for 4 h. The resin and glass beads were filtered and the TFA was removed from the filtrate in vacuo. Diethyl ether was poured on the residue and the peptide precipitated, was filtered, washed with ether and dried. The crude peptide was purified by the standard preparative HPLC chromatography procedure.

The peptides were then purified by reverse-phase liquid chromatography using a Waters Pre-Pak (Delta-Pak C$_{18}$) column on a Waters Delta Prep 4000 system equipped with a Waters 484 ultraviolet detector. Purification was achieved by equilibrating the column with 0.1% TFA in water and developing with a linear gradient of acetonitrile from 1–40% in 20 minutes at a flow rate of 20 mL/min at 220 nm. Samples were collected manually and checked for purity on a Waters analytical HPLC system (including a 600E pump and system controller, a 494 photodiode array detector, and a 712 WISP autosampler) utilizing a Waters Radial-Pak (Delta-Pak C$_{18}$) column. A flow rate of 2.5 mL/min was employed using a 0.1% TFA/acetonitrile gradient from 10–60% ACN in 10 minutes at 200 nm.

Method C: Dimeric Nonapeptides (amidebridged)

Synthesis of protected 2,3-diaminopropionic acid: (S)-2-((tert-butoxycarbonyl)amino)-3-((9H-Floren-9-ylmethoxy) carbonyl) amino)propionic acid: A solution of 10 g (42 mMol) of N-α-CBZ-diamino)propionic acid (Fluka, Catalogue 1990–91 p1368 No. 96085) in 75 mL of 1,4-dioxane was treated with 75 mL of 1N aqueous sodium hydroxide, followed by 9.1 g (35 mMol) of 9-fluorenylmethyl chloroformate (Aldrich, Catalogue 1992–93 p620 No. 16,051-2) and 5 g (15 mMol) of N-(9-fluorenylmethoxycarbonyloxy) succinimide (Aldrich, Catalogue 1992–93 p620 No. 28,950-7). The resulting mixture was stirred an 25° C. for 4 h and then acidified to pH 2 with concentrated aqueous hydrochloric acid and extracted with ether. Drying over magnesium sulfate and evaporation of the volatiles afforded a white foam, which was redissolved in 150 mL of 30% hydrogen bromide in acetic acid. After stirring for 1 h at 25° C., the volatiles were removed in vacuo and residual acetic acid was co-evaporated three times with toluene. Trituration with ether afforded a beige solid which was slurried in 1,4-dioxane (75 mL). Triethylamine (12.5 mL) was added, followed by di-t-butyldicarbonate (13.08 g, 60 mMol) and ether (75 mL), and the slurry was stirred for 3 h at 25° C. The resulting mixture was diluted with ether and extracted with 1N aqueous hydrochloric acid. The organic layer was washed with water, dried over magnesium sulfate and the volatiles were removed in vacuo. Recrystallization from 15% dichloromethane-hexane afforded the desired bisprotected diaminopropionic acid as a white powder. $^1$H NMR (300 MHz) δ 1.46 (9H), 3.64 (2H), 4.20 (1H), 4.29 (1H), 4.42 (2H), 5.46 (1H), 5.88 (1H), 7.31 (2H), 7.33 (2H), 7.57 (2H), 7.76 (2H); anal. calcd. C:64.78 H:6.15 N:6.57. Found C:64.71 H:6.18 N:6.55

Synthesis of Dimeric Nonapeptides:

Dimeric peptides were assembled on solid phase using standard BOC protocols. Sidechain protection of diaminopropionic acid and Asp/Glu was accomplished using Fmoc and 9-fluorenylmethylester groups respectively. Before deprotection of the terminal Boc group, the 9-Florenyl derived sidechain protections were removed by treatment with 50% piperidine in dichloromethane. BOF (2 equivalents) in DMF was added and the mixture was shaken at 25° C. for 48 h or until a negative Ninhydrin test was observed. The resulting peptides were further processed, isolated, and characterized in the usual manner (treatment with HF, purification by preparative HPLC, characterization by FAB-MS and amino acid analysis).

FAB-MS analysis:

Fast atom bombardment (FAB) mass spectra were obtained on a VG 70SQ mass spectrometer of EBQQ geometry using a VG 11-250J Data System for data acquisition. The mass spectrometer was operated at seven kilovolts accelerating potential and a resolution of 1000 (10% valley definition). The FAB gun used in the experiments was Io Tech FAB 11N operating at seven kilovolts potential and one milliamperes current. Xenon was used as the bombardment gas at a pressure of $1\times10^{-5}$ millibars source pressure. The sample of interest was dissolved in glycerol prior to analysis by FAB-MS.

The invention is illustrated, but not limited, by the following examples:

The method of synthesis of each peptide is indicated. All peptides were purified by HPLC. Analytical data and the structure of each Example are shown in the Table.

EXAMPLE 1

IleAsnProAibTyrAgrLeuArgTyr-NH$_2$
(SEQ.ID.No:8)

The peptide was synthesized by method A. Analytical data in the Table. Purification by HPLC.

EXAMPLE 2

IleAsnPro(O-MethylThr)TyrArgLeuArgTyr-NH$_2$
(SEQ.ID.No:9)

The peptide was synthesized by method A. Analytical data in the Table.

EXAMPLE 3

IleAsnProAib[O-(2,6-Dichlorobenzyl)Tyr]ArgLeuArgTyr-NH$_2$ (SEQ.ID.No:10)

Synthesis by method B.

EXAMPLE 4

IleAsnProIleTyrArgLeuArg[O-(2,6-Dichlorobenzyl)-Tyr]-NH$_2$ (SEQ.ID.No:11)

Synthesis by method B.

EXAMPLE 5

IleAsnProIle[O-(2,6-Dichlorobenzyl)Tyr]ArgLeuArgTyr-NH$_2$ (SEQ.ID.No:12)

Synthesis by method B.

EXAMPLE 6

Synthesis of IleCysProCysTyrArgLeuArgTyr-NH$_2$, Cyclic(2,2'), (4,4')-Disulfide Dimer and IleCysProCysTyrArgLeuArgTyr-NH$_2$,Cyclic(2,4'), (4,2')-Disulfide Dimer (SEQ.ID.No:6)

The reduced peptide IleCysProCysTyrArgLeuArgTyr-NH$_2$ (SEQ.ID.No:6) was assembled in the peptide synthesizer as described above in Method A, cleaved from the resin with liquid HF and purified by preparative HPLC. This preparation was a single peak on analytical HPLC and eluted at 7.53 min at standard conditions. The peptide also was observed co 100% pure on capillary zone electrophoresis (CZE). The correct structure was confirmed by Fab-MS. (MH$^+$=1185.7). This peptide gives a yellow colour with the Ellman reagent, indicating the presence of a —SH moiety in the peptide. Forty milligrams of the peptide were dissolved in 500 ml of 20 mM sodium phosphate buffer (pH 8.5) and a 0.1M solution of potassium ferricyanide was added in 100 microliter portions until the colour of the peptide solution stayed yellow. The solution was then lyophilized and purified by preparative HPLC to yield 10 milligrams of a solid that consisted of two items on analytical HPLC. The first peak (23% of the solid) eluted at 7.46 min under standard conditions. The second peak (77% of the solid) eluted at 7.79 min. CZE of Peak #1 yielded one peak (100% purity based on CZE). Peak #2 yielded two items on CZE ration (1:2). This preparation does not yield a yellow colour with the Ellman test i.e. no free —SH groups are present. FAB-MS of Peak #2 indicates that the two peptides are the two dimer types each of which contain the same monomers but have the monomers arranged in either the same or opposing orientations respectively (MH$^+$=2367.4).

EXAMPLE 6(a)

Synthesis of IleCysProCysTyrArgLeuArgTyr-NH$_2$, Cyclic (2,2'),(4,4')-Disulfide Dimer (SEQ.ID.No:6) and IleCysProCysTyrArgLeu-ArgTyr-NH$_2$,Cyclic(2, 4'),(4,2')-Disulfide Dimer (SEQ.ID.No:6)

The peptide was assembled by the automated Boc-protection procedure as described above in Method A, on a 0.5 mM scale using the standard sidechain protection groups except for cysteine which was introduced as Boc-Cys(S-Fmoc). After the deprotection of the last Boc-group, the peptide resin was created with a solution of 50% piperidine in DMF for three hours while constantly saturating the solution with oxygen. Cleavage of the peptide from the resin with liquid HF yielded 200 mg of crude peptide which, after purification by preparative HPLC, gave 50 mg pure product. This material was indistinguishable from Peak #2 obtained in Example 6 as shown by HPLC and FAB-MS. CZE indicated the presence of the same two products as obtained in Peak #2 of Example 6.

EXAMPLE 7

IleAspProDprTyrArgLeuArgTyr-NH$_2$,Cyclic(2,4'), (2',4)-Diamide (SEQ.ID.No:7)

Synthesized by method C.

EXAMPLE 8

IleDprProAspTyrArgLeuArgTyr-NH$_2$,Cyclic(2,4'), (2',4)-Diamide (SEQ.ID.No:5)

Synthesized by Method C.

EXAMPLE 9

IleGluProDprTyrArgLeuArgTyr-NH$_2$,Cyclic(2,4'), (2',4)-Diamide (SEQ.ID.No:4)

Synthesized by Method C.

EXAMPLE 10

IleAsnProIlePheArgLeuArgTyr-NH$_2$
(SEQ.ID.No:13)

Synthesized by Method A.

EXAMPLE 11

IleAsn(3,4-DehydroPro)IleTyrArgLeuArgTyr-NH$_2$
(SEQ.ID.No:14)

Synthesized by Method A.

EXAMPLE 12

(IleAsnProCysTyrArgLeuArgTyr-NH$_2$)$_2$
(SEQ.ID.No:15)

The monomeric structure was prepared using Method A, FAB-MS (MH+=1197.0), capillary zone electrophoresis, and amino acid analysis (Arg: 2.01, Asp: 0.83, Ile: 0.96, Leu: 1.00, Pro: 1.44, Tyr: 1.84) verified this structure. Approximately 100 mg ($8.4 \times 10^{-5}$ moles) of the monomer was dissolved in 50 mL of Na$_2$HPO$_4$ buffer (pH=8). A 0.1 solution of aqueous K$_4$Fe(SCN)$_6$ (10×100 µL, $1 \times 10^{-4}$ moles) was added and stirred until the yellow colour no longer dissipated. This material was lyophilized and purified by C18 preparative HPLC as described previously. This dimeric structure was verified by FAB-MS (MH+=2391.6), capillary zone electrophoresis, and amino acid analysis (Arg: 1.98, Asp: 1.14, Ile: 0.87, Leu: 1.03, Pro: 1.00, Tyr: 1.97).

EXAMPLE 13

(IleCysProIleTyrArgLeuArgTyr-NH$_2$)$_2$
(SEQ.ID.No:16)

The monomeric structure was prepared using Method A, FAB-MS (MH+=1196.1), capillary zone electrophoresis, and amino acid analysis (Arg: 2.08, Ile: 1.28, Leu: 1.00, Pro: 1.31, Tyr: 1.80) verified this structure. Approximately 100 mg ($8.4 \times 10^{-5}$ moles) of the monomer was dissolved in 50 mL of Na$_2$HPO$_4$ buffer (pH=8). A 0.1M solution of aqueous K$_4$Fe(SCN)$_6$ (10×100 µL, $1 \times 10^{-4}$ moles) was added and stirred until the yellow colour no longer dissipated. This material was lyophilized and purified by C18 preparative HPLC as described previously. This dimeric structure was verified by FAB-MS (MH+=2374.1), capillary zone electrophoresis, and amino acid analysis (Arg: 2.76, Ile: 1.56, Leu: 1.00, Pro: 1.18, Tyr: 1.60).

EXAMPLE 14

IleAsnPro TyrArgLeuArgTyr-NH$_2$ (SEQ.ID.No:17)
Pim IleAsnPro TyrArgLeuArgTyr-NH$_2$
(SEQ.ID.No:17)

(Pim=2,6-Diaminopimelic Acid L,D)

Into 80 mL of 5% Na$_2$CO$_3$ and 50 mL 1,4-dioxane, (±)-2,6-diaminopimelic acid (5 g, 26.3 mmoles, Aldrich) was dissolved and cooled to 0° C. A solution containing 24.2 mL (105.2 mmoles, Aldrich) of di-tert-butyl dicarbonate in dioxane was added dropwise. After addition was complete, the mixture was allowed to warm to room temperature and stirred for 16 h. The dioxane was then removed in vacuo, and the aqueous was acidified to pH=1 with 1N HCl. A colourless oil was obtained and dissolved in 10 mL of ethyl acetate. To this, 10.6 mL (52.6 mmoles, Aldrich) of dicyclohexylamine was added. The mixture was diluted with 250 mL of diethyl ether and cooled overnight. A white solid was filtered and dried to yield 9.6 g (48.2%) and used without further purification. NMR dmso (ppm): 1.0–2.0 m, 44H; 1.4 s, 18H; 3.5–3.6m, 2H; 6.0–6.1m, 2H.

A sample (0.5 mmoles) of p-methylbenzhydrylamine.HCl resin (obtained as before) (MBHA) was loaded onto an Applied Biosystems Inc. Model 430A Peptide Synthesizer and the following amino acids (1.0 mmole each) were coupled to the MBHA resin using a programme to suit a BOP coupling procedure as described by Dung Le Nguyen et al (ibid): Boc-Tyr(2-Br-CBZ), Boc-Arg(Tos), Boc-Leu, Boc-Arg(Tos), and Boc-Tyr(2-Br-CBZ). The MBHA resin was then deprotected utilizing 50% trifluoroacetic acid (TFA)/CH$_2$Cl$_2$. The resin was removed from the ABI-430A and manually shaken for 1 h with 184 mg (0.25 mmoles) of Boc(L.D)-Pim-DCHA, 112 mg (0.25 mmoles) of BOP reagent, and 25 µL (0.25 mmoles) of N-methylimidazole (Aldrich). The resin was once again deprotected with TFA and returned to the ABI-430A, where these remaining amino acids were added: Boc-Pro, Boc-Asn(Xan), and Boc-Ile.

The peptide was cleaved form the resin with HF/1% anisole at 0° C., extracted with 10% aqueous acetic acid and lyophilized. Purification was performed on a Waters Prep-Pak Delta-Pak C18 column eluting the peptide with acetonitrile from 0.1% TFA/H$_2$O. HPLC purity was verified (one peak only) using an analytical system identical to the preparative HPLC system described above.

FAB-MS showed the correct peptide at 2342.7 (MH+). Amino acid analysis corroborated this finding with the following results: Arg (4.29), Asp (1.43), Ile (1.45), Leu (2.00), Pro (2.08), and Tyr (3.91).

EXAMPLE 15

IleGluProOrnTyrArgLeuArgTyr-NH$_2$,Cyclic(2,4'),
(2',4)-Diamide (SEQ.ID.No:2)

Synthesized by Method A. Nocy-Glu(OFm) was purchased by Bachem, Inc. (Torrance, Calif.). Alpha-boc-delta-fmoc-ornithine was synthesized from alpha-boc-ornithine (obtained from Bachem Bioscience, Inc., Philadelphia, Pa.) using the same procedure described in Method C for alpha-boc-gamma-fmoc-diaminopropionic acid. $^1$H NMR (300 mHz) d 1.45 (9H), 1.47–1.99 (4H), 3.23 (2H), 4.21 (1H), 4.42 (2H), 5.02 (1H), 5.10 (1H), 6.00 (1H), 7.22–7.79 (8H).

Anal. Calcd. C: 66.06, H: 6.65, N: 6.16. Found C: 65.93, H: 6.69, N: 5.97.

EXAMPLE 16

IleAspProOrnTyrArgLeuArgTyrNH$_2$,Cyclic(2,4'),(2',4)-Diamide (SEQ.ID.No:3)

Synthesized as described in Example 15.

EXAMPLE 17

TyrIleAsnLeuIleTyrArgLeuArgTyr-NH$_2$
(SEQ.ID.No:18)

Synthesized by Method A.

EXAMPLE 18 desNH$_2$TyrIleAsnLeuIleTyrArgLeuArgTyr-NH$_2$
(SEQ.ID.No:18)

Synthesized by Method A.

BIOLOGICAL EVALUATION

Radioreceptor Binding Assay

Rat brain membranes were incubated with $^3$H-NPY up to equilibrium at 37° C. in the presence of several peptides at different concentrations and in a final volume of 1 ml.

Non-specific binding was determined by adding 100 nM of cold NPY. At the end of the incubation period the samples were either filtered (GF/C filter), or 0.5 ml of cold incubation buffer was added and the tubes centrifuged at 15,000 g for 10 min. The supernatant was discarded and the pellet or filters resuspended and counted by liquid scintillation. Results were processed using a computer programme that calculated $IC_{50}$, Kd, $B_{max}$ and Hill coefficient by linear regression. $IC_{50}$ results where available are shown in column (a) of the Table.

Intracellular Calcium Measurements

Human erythroleukemic (HEL) cells were loaded with Fura-2 (1 µM for 1 h), washed and then placed in a cuvette ($5\times10^5$ cells in 2.5 ml) and excited simultaneously at 340 and 380 nm in a SLM spectrofluorometer. Fluorescence changes after the addition of NPY and/or peptide analogs were followed by recording emission at 510 nm. Calcium concentrations can be determined through a computer programme by using the ratio of fluorescence 340/380 nm. The agonistic activity of peptide analogs was tested by recording the fluorescence induced upon stimulation of the cells with 100 nM of the peptide and the antagonistic activity by observing the decrease in fluorescence induced by 5 nM NPY in the presence of the analog The results where available are indicated in column (c) of the Table.

The inhibition of the increase in the HEL cell intracellular calcium (induced by 5 nM NPY) achieved by 100 nM concentrations of each compound is shown in column (b) of the Table.

Isolated Perfused Rat Kidney Preparation

Male CD rats (200–400 g) are anaesthetised with a mixture of Acepromazine (2.8 mg/kg) and Kenamine (112 mg/kg) injected i.p. The rat's abdomen is opened through the midline. The renal arteries and descending aorta are cleaned and, with minimal disruption of blood flow, one kidney is cannulated through the proximal renal artery using a stainless steel 20G blunt-tipped needle attached to Tygon tubing and a peristaltic pump. As soon as the first ligature is complete and perfusion of the kidney starts (10 ml/min) and the kidney is removed from the animal and placed in a constant temperature perfusion chamber. The perfusion pressure is followed by an on-line Statham pressure transducer and changes recorded in a Grass Polygraph.

Administration of Drugs: Neuropeptide Y and other agonists are administered by a single bolus injection (0.1 ml) through an injection port situated about 6 inches from the tip of the needle (approximately 0.3 ml, total volume). Antagonists are infused during 5 min (0.15 ml/min) into the kidney through an injection port situtated before the perfusion pump to allow for good mixing and constant concentration (dilution of 0.15 ml into 10 ml).

Perfusion Buffer (mM): NaCl 122; KCl 4.73; $NaHCO_3$ 15.5; $KH_2PO_4$ 1.19; $CaCl_2$ 2.5; $MgCl_2$ 1.19; Glucose 11.5 and 1% BSA pH 7.4. The buffer is constantly bubbled with 95%, $O_2$, 5%, $CO_2$.

Results: Using the above experimental procedure we have determined the $IC_{50}$ for the inhibition of the NPY-induced increase of perfusion pressure for:

|  | $IC_{50}$(nM) |
|---|---|
| IleCysProCysTyrArgLeuArgTyr-$NH_2$ Cyclic (2,2'),(4,4')-Disulfide Dimer (SEQ.ID.No:6) and | 2.5 |
| IleCysProCysTyrArgLeuArgTyr—$NH_2$ Cyclic (2,4'),(4,2')-Disulfide Dimer (SEQ.ID.No:6) | 2.5 |
| IleGluProDprTyrArgLeuArgTyr—$NH_2$ Cyclic (2,4'),(2',4)-Diamide (SEQ.ID.No:4) | 0.5 |

TABLE

| EXAMPLE NO. | STRUCTURE | BRAIN $IC_{50}$ (µm) (a) | HEL CELLS % INHIB (b) | % Fluor (c) | $IC_{50}$ (µm) (d) | $MH^+$ (FAB)—MS | AAA |
|---|---|---|---|---|---|---|---|
| 1. | IleAsnProAibTyrAgr LeuArgTyr—$NH_2$ (SEQ. ID. No:8) | 0.25 | 100 | 0 | 0.010 | 1178.9 | Arg (1.79), Asp (0.69), Ile (0.70), Leu (1.00), Pro (0.73), Tyr (1.81) |
| 2. | IleAsnPro(O-MethylThr) TyrArgLeuArgTyr—$NH_2$ (SEQ. ID. No:9) | 0.28 | 100 | 0 | 0.005 | 1208.6 | Arg (1.80), Asp (0.98), Ile (0.92), Leu (1.00), Pro (1.02), Tyr (1.75) |
| 3. | IleAsnProAib[O—(2,6-Dichlorobenzyl)Tyr]Arg LeuArgTyr—$NH_2$ (SEQ. ID. No:10) | 0.35 | 100 | 0 | 0.008 | 1337.4 | Arg (2.04), Asp (0.09), Ile (0.16), Leu (1.00), Pro (0.19), Tyr (1.91) |
| 4. | IleAsnProIleTyrArg LeuArg[O—(2,6-Dichlorobenzyl)—Tyr]—$NH_2$ (SEQ. ID. No:11) | 1.4 | 100 | 0 | 0.010 | 1366.8 | Arg (1.94), Asp (0.29), Ile (1.19), Leu (1.00), Pro (1.03), Tyr (1.68) |
| 5. | IleAsnProIle[O—(2,6-Dichlorobenzyl)Tyr] ArgLeuArgTyr—$NH_2$ (SEQ. ID. No:12) | 0.05 | 100 | 0 | 0.0025 | 1365.9 | Arg (2.02), Asp (0.88), Ile (1.03), Leu (1.00), Pro (0.40), Tyr (1.94) |
| 6. | IleCysProCysTyrArg LeuArgTyr—$NH_2$ Cyclic (2,2'),(4,4')-Dilsulfide Dimer and IleCysProCysTyrArg LeuArgTyr—$NH_2$ Cyclic (2,4'),(4,2')- | 0.25 | 100 | 0 | 0.002 | 2367.5 | Arg (3.88), Ile (1.28), Leu (2.00), Pro (2.12), Tyr (3.60) |

TABLE-continued

| | | BRAIN HEL CELLS | | | | | |
|---|---|---|---|---|---|---|---|
| EXAMPLE NO. | STRUCTURE | $IC_{50}$ (μm) (a) | % INHIB (b) | % Fluor (c) | $IC_{50}$ (μm) (d) | $MH^+$ (FAB)—MS | AAA |
| 7. | Disulfide Dimer (SEQ. ID. No:6) IleAspProDprTyrArgLeu ArgTyr—$NH_2$ Cyclic (2,4'),(2',4)- Diamide (SEQ. ID. No:7) | 0.015 | 100 | 0 | 0.0015 | 1162.2* [2324.8] | Arg (1.87), Asp (0.82), Ile (0.81), Leu (1.00), Pro (1.24), Tyr (1.91) |
| 8. | IleDprProAspTyrArg LeuArgTyr—$NH_2$ Cyclic (2,4'),(2',4)- Diamide (SEQ. ID. No:5) | 0.0075 | 100 | 0 | 0.0025 | 1162.5* [2324.8] | Arg (1.90), Asp (1.09), Ile (0.29), Leu (1.00), Pro (1.23), Tyr (2.05) |
| 9. | IleGluProDprTyrArg LeuArgTyr—$NH_2$ Cyclic (2,4'),(2',4)- Diamide (SEQ. ID. No:4) | 0.001 | 100 | 0 | 0.00029 | 2353.9 | Arg (1.89), Glu (0.81), Ile (0.83), Leu (1.00), Pro (1.18), Tyr (1.97) |
| 10. | IleAsnProIlePheArg LeuArgTyr—$NH_2$ (SEQ. ID. No:13) | 0.47 | 100 | 0 | 0.01 | 1191.0 | Arg (2.00), Asp (0.91), Ile (1.98), Leu (1.05), Phe (0.96), Pro (1.06), Tyr (1.00) |
| 11. | IleAsn(3,4-Dehydro-Pro)IleTyrArgLeuArg Tyr—$NH_2$ (SEQ. ID. No:14) | 0.036 | 100 | 0 | 0.01 | 1205.0 | Arg (1.85), Asp (0.90), Ile (1.66), Leu (1.00), Tyr (1.66) |
| 12. | (IleAsnProCysTyrArg LeuArgTyr—$NH_2)_2$ (SEQ. ID. No:15) | 0.005 | 100 | 0 | 0.0005 | 2391.6 | Arg (3.97), Asp (2.28), Ile (1.75), Pro (2.00), Tyr (3.94), Leu (0.07) (value for dimer) |
| 13. | (IleCysProIleTyrArg LeuArgTyr—$NH_2)_2$ (SEQ. ID. No:16) | 0.035 | 100 | 0 | 0.00075 | 2374 | Arg (3.52), Ile (3.13), Leu (2.00), Pro (2.36), Tyr (3.21) (value for dimer) |
| 14. | IleAsnPro\TyrArgLeuArgTyr—$NH_2$ \Pim/ IleAsnPro/TyrArgLeuArgTyr—$NH_2$ (SEQ. ID. NO:17) (Pim = 2,6-Diaminopimellic acid L, Q) | 0.0019 | 100 | 0 | 0.005 | 2342.7 | Arg (4.29), Asp (1.43), Ile (1.45), Leu (2.00), Pro (2.08), Tyr (3.9) |
| 15. | IleGluProOrnTyrArgLeu ArgTyr—$NH_2$ Cyclic (2,4'),(2',4)- Diamide (SEQ. ID. No:2) | <0.0001 | 100 | 0 | 0.00025 | 1295.2* [2408.0] | Arg (2.07), Glx (0.96), Ile (0.93), Leu (1.00), Pro (1.06), Tyr (1.67) |
| 16. | IleAspProOrnTyrArgLeu ArgTyr—$NH_2$ Cyclic (2,4'),(2',4)- Diamide (SEQ. ID. No:3) | <0.0001 | 100 | 0 | 0.00025 | 1191.2* [2380.8] | Arg (2.09), Asx (0.56), Ile (0.58), Leu (1.00), Pro (1.36), Tyr (2.17) |
| 17. | TyrIleAsnLeuIleTyrArg LeuArgTyr—$NH_2$ (SEQ. ID. No:8) | 0.015 | 100 | 10 | 0.00075 | 1386.3 | Arg (1.96), Asx (1.09), Ile (1.39), Leu (2.00), Tyr (2.64) |
| 18. | des$NH_2$TyrIleAsnLeuIle TyrArgLeuArgTyr—$NH_2$ (SEQ. ID. No:18) | 0.017 | 62 | 28 | N/A | 1371.7 | Arg (2.20), Asp (0.79), Ile (1.93), Leu (2.00), Tyr (1.96) |

We claim:

1. A peptide of formula (I), or a multimer thereof or a salt thereof:

$$R_1-X_5ArgX_6ArgX_5-R_2 \quad (I) \text{ (SEQ.ID.No:1)}$$

where $R_1 = X_1X_2X_3X_4$ in which $X_1$ = Ile, TyrIle, or desNH$_2$TyrIle
$X_2$ = Asn, Asp, Cys, Dpr, Glu or Gly
$X_3$ = Leu, Pro or 3,4-DehydroPro
$X_4$ = Aib, Asp, Cys, Dpr, Glu, Gly, Ile, Orn, Tyr or O-MethylThr
$X_5$ = Phe, Tyr or [O-(2,6-Dichlorobenzyl)Tyr]
$X_6$ = Phe or Leu where $R_2 = -(CH_2)_nCH_3, -(CH_2)_nNH_2$ or

in which n=0–4.

2. A peptide according to claim 1, wherein $X_2$ is selected from Dpr, Cys, Asp and Glu.

3. A peptide according to claim 1, wherein $X_3$ is Pro.

4. A peptide according to claim 1, wherein $X_4$ is selected from Asp, Cys, Dpr and Orn.

5. A peptide according to claim 1, wherein $X_5$ is Tyr.

6. A peptide according to claim 1, wherein $R_2$ is $-(CH_2)_nNH_2$.

7. A multimer of a peptide according to claim 1.

8. A multimer according to claim 7, wherein the multimer is a dimer.

9. A multimer according to claim 7, wherein the peptides containing Gly residues are bridged at the alpha positions to form one or more bridges, by one or more groups selected from

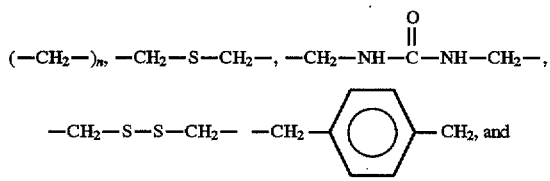

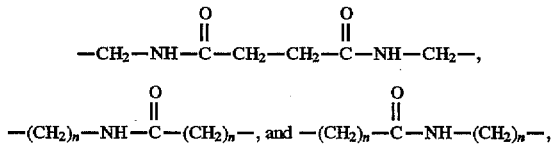

wherein n=0–4.

10. A peptide, multimer thereof or salt thereof, the peptide having a structure selected from:

IleGluProOrnTyrArgLeuArgTyr-NH$_2$,Cyclic(2,4'),(2',4)-Diamide (SEQ.ID.No:2),

IleAspProOrnTyrArgLeuArgTyr-NH$_2$,Cyclic(2,4'),(2',4)-Diamide (SEQ.ID.No:3),

IleGluProDprTyrArgLeuArgTyr-NH$_2$,Cyclic(2,4'),(2',4)-Diamide (SEQ.ID.No:4), and IleDprProAspTyrArgLeuArgTyr-NH$_2$,Cyclic(2,4'),(2',4)-Diamide (SEQ.ID.No:5).

11. A peptide, multimer thereof or salt thereof, the peptide having a structure selected from:

IleCysProCysTyrArgLeuArgTyr-NH$_2$,Cyclic(2,2'),(4,4')-Disulfide Dimer (SEQ.ID.No:6), and IleCysProCysTyrArgLeuArgTyr-NH$_2$,Cyclic(2,4'),(4,2')-Disulfide Dimer (SEQ.ID.No:6).

12. A peptide, multimer thereof according to claim 10 or salt thereof, the peptide having the structure:

IleGluProDprTyrArgLeuArgTyr-NH$_2$,Cyclic(2,4'),(2',4)-Diamide (SEQ.ID.No:4).

13. A peptide, multimer thereof according to claim 10 or salt thereof, the peptide having the structure:

IleDprProAspTyrArgLeuArgTyr-NH$_2$,Cyclic(2,4'),(2',4)-Diamide (SEQ.ID.No:5).

14. A pharmaceutically acceptable salt of a peptide or multimer according to claim 1.

15. A pharmaceutical formulation comprising a peptide or multimer according to claim 1, or a pharmaceutically acceptable salt thereof, together with an acceptable carrier therefor.

16. A method for the treatment of cardiovascular disorders, hypertension, hypertensive crisis, vasospasm, cerebral or coronary vasospasm, and glaucoma, which requires administering to a human being, a therapeutically effective, non-toxic amount of a peptide or multimer or salt thereof according to claim 1.

* * * * *